(12) United States Patent
Hohlbein

(10) Patent No.: US 7,478,959 B2
(45) Date of Patent: Jan. 20, 2009

(54) ORAL CARE TOOTHBRUSH

(75) Inventor: Douglas J. Hohlbein, Pennington, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 11/314,716

(22) Filed: Dec. 21, 2005

(65) Prior Publication Data

US 2006/0165473 A1 Jul. 27, 2006

Related U.S. Application Data

(63) Continuation-in-part of application No. 10/843,135, filed on May 11, 2004, now Pat. No. 7,331,731, which is a continuation-in-part of application No. PCT/US03/27455, filed on Sep. 4, 2003, said application No. 11/314,716 is a continuation of application No. 29/231,483, filed on Jun. 6, 2005, now Pat. No. Des. 532,607, which is a continuation of application No. 29/213,754, filed on Sep. 23, 2004, now Pat. No. Des. 532,202, which is a continuation-in-part of application No. 10/843,135, filed on May 11, 2004, now Pat. No. 7,331,731, which is a continuation-in-part of application No. PCT/US03/27455, filed on Sep. 4, 2003, said application No. 11/314,716 is a continuation of application No. 29/231,487, filed on Jun. 6, 2005, now Pat. No. Des. 528,803.

(60) Provisional application No. 60/408,321, filed on Sep. 5, 2002.

(51) Int. Cl.
*A47L 13/22* (2006.01)

(52) U.S. Cl. .................. 401/132; 401/286; 401/288

(58) Field of Classification Search ......... 401/183–186, 401/270, 277, 278, 279, 286, 288, 132–135, 401/282, 284, 285, 287; D4/104, 110, 111, D4/112

See application file for complete search history.

(56) References Cited

U.S. PATENT DOCUMENTS

| 792,471 | A | | 6/1905 | Smith |
| 846,900 | A | | 3/1907 | Bloom |
| 876,185 | A | | 1/1908 | Hillman |
| 1,214,556 | A | | 2/1917 | Vene et al. |
| 1,256,662 | A | * | 2/1918 | Cleman et al. ............... 401/277 |
| 1,411,681 | A | | 4/1922 | Burlew |
| 1,500,722 | A | | 7/1924 | Roush |
| 1,575,317 | A | | 3/1926 | Carmichael |
| 1,602,531 | A | | 10/1926 | Itoh |
| 1,784,986 | A | | 12/1930 | Eisenberg |

(Continued)

FOREIGN PATENT DOCUMENTS

CH 664 271 A5 2/1988

(Continued)

*Primary Examiner*—David J Walczak
(74) *Attorney, Agent, or Firm*—Donald L. Traut

(57) ABSTRACT

An oral care toothbrush includes a head mounted to one end of the handle containing a plurality of oral care elements. An oral care accessory is mounted to the opposite end of the handle. An oral care material dispenser is mounted in the head within the cleaning field defined by the oral care elements. The toothbrush is preferably made of small size and of lightweight so as to be readily portable for use away from the home.

17 Claims, 5 Drawing Sheets

U.S. PATENT DOCUMENTS

| | | | |
|---|---|---|---|
| 1,796,367 A | | 3/1931 | Grove |
| 1,797,946 A | * | 3/1931 | Eichel .................. 401/184 |
| 1,811,833 A | | 6/1931 | Simon |
| RE19,006 E | | 11/1933 | Graves |
| 1,950,767 A | | 3/1934 | Abbott |
| 1,968,303 A | | 7/1934 | McMath |
| 1,995,374 A | | 3/1935 | Young |
| 2,077,758 A | | 4/1937 | Johnson et al. |
| 2,233,831 A | | 3/1941 | Burke |
| 2,241,584 A | | 5/1941 | Cohen |
| 2,259,928 A | * | 10/1941 | Eaton .................. 401/184 |
| 2,262,982 A | * | 11/1941 | Wolcott .................. 15/167.1 |
| 2,307,493 A | * | 1/1943 | Davidson .................. 401/268 |
| 2,386,085 A | | 10/1945 | Babel |
| 2,649,959 A | | 8/1953 | Hallahan |
| 2,710,982 A | | 6/1955 | Gillem |
| 2,736,917 A | | 3/1956 | Young |
| 2,778,045 A | | 1/1957 | Bly et al. |
| 2,793,381 A | * | 5/1957 | McWhorter .................. 401/145 |
| 3,068,571 A | | 12/1962 | Thompson |
| 3,078,856 A | | 2/1963 | Bender et al. |
| 3,103,935 A | | 9/1963 | Woodrow |
| 3,148,684 A | * | 9/1964 | Keeler .................. 401/140 |
| 3,165,776 A | | 1/1965 | Tuseth |
| 3,301,267 A | * | 1/1967 | Gerardi et al. .................. 401/155 |
| 3,432,245 A | * | 3/1969 | Hudson .................. 401/132 |
| 3,458,268 A | | 7/1969 | Wozab et al. |
| 3,491,396 A | | 1/1970 | Granieri, Jr. et al. |
| 3,536,410 A | | 10/1970 | Wargoe |
| 3,609,789 A | | 10/1971 | Slater |
| 3,698,405 A | | 10/1972 | Walker |
| 3,917,420 A | | 11/1975 | Watson |
| 4,194,290 A | | 3/1980 | Vallhonrat |
| 4,292,304 A | | 9/1981 | Barels et al. |
| D278,863 S | | 5/1985 | Bradley |
| 4,864,676 A | | 9/1989 | Schaiper |
| 4,911,187 A | | 3/1990 | Castillo |
| 5,061,106 A | | 10/1991 | Kent |
| 5,133,971 A | | 7/1992 | Copelan et al. |
| 5,366,310 A | * | 11/1994 | Armelles Flors ............ 401/132 |
| 5,390,984 A | | 2/1995 | Boucherie et al. |
| 5,393,796 A | | 2/1995 | Halberstadt et al. |
| 5,522,109 A | * | 6/1996 | Chan .................. 15/106 |
| 5,533,791 A | | 7/1996 | Boucherie |
| 5,609,890 A | | 3/1997 | Boucherie |
| D378,711 S | | 4/1997 | Occhetti |
| 5,860,183 A | | 1/1999 | Kam |
| 5,888,002 A | | 3/1999 | Femstersheib |
| 6,004,059 A | | 12/1999 | Zaccaria |
| 6,135,274 A | | 10/2000 | James |
| 6,321,407 B1 | | 11/2001 | Weihrauch |
| 6,397,860 B1 | | 6/2002 | Hill, II |
| 6,401,291 B1 | * | 6/2002 | Lee .................. 15/167.1 |
| 6,524,023 B2 | | 2/2003 | Andersen |
| 6,526,993 B1 | | 3/2003 | Wagner |
| 6,602,013 B2 | | 8/2003 | Clark |
| 2002/0175101 A1 | | 11/2002 | Albert |
| 2003/0188761 A1 | | 10/2003 | Garcia et al. |

FOREIGN PATENT DOCUMENTS

| | | |
|---|---|---|
| DE | 3529953 | 3/1987 |
| DE | 4127429 | 2/1993 |
| DE | 42 31 817 A1 | 3/1994 |
| DE | 19531368 | 2/1997 |
| DE | 19842984 | 8/2000 |
| EP | 0 475 314 A1 | 3/1992 |
| EP | 0 481 926 B1 | 4/1992 |
| EP | 0 872 195 | 10/1998 |
| FR | 2 646 068 A | 10/1990 |
| FR | 2 654 598 A | 5/1991 |
| FR | 2 754 436 A | 4/1998 |
| FR | 2 772 569 A | 6/1999 |
| FR | 2 822 658 | 10/2002 |
| FR | 2 822 658 A1 | 10/2002 |
| GB | 228460 | 2/1925 |
| GB | 746649 | 3/1956 |
| GB | 2351015 | 12/2000 |
| GB | 2388529 | 11/2003 |
| GB | 2 394 653 A | 5/2004 |
| JP | 10-216158 | 8/1998 |
| JP | 2003 245133 A | 9/2003 |
| WO | WO 99/60886 | 12/1999 |
| WO | WO 02/26079 A1 | 4/2002 |
| WO | WO 02/34083 A1 | 5/2002 |
| WO | WO 02/058508 A2 | 8/2002 |
| WO | WO 03/037210 A1 | 5/2003 |
| WO | WO 2004/021914 | 3/2004 |
| WO | WO 2004/021914 A2 | 3/2004 |
| WO | WO 2004/010821 A1 | 5/2004 |
| WO | WO 2005/110149 | 11/2005 |

\* cited by examiner

ORAL CARE TOOTHBRUSH

This is (1) a continuation-in-part of U.S. application Ser. No. 10/843,135, filed May 11, 2004 now U.S. Pat. No. 7,331,731, which is a continuation-in-part of International application PCT/US03/27455, filed Sep. 4, 2003, which claimed priority to U.S. Application 60/408,321, filed Sep. 5, 2002; (2) a continuation of U.S. application Ser. No. 29/231,483, filed Jun. 6, 2005, now U.S. Pat. No. D532,607, which is a continuation of U.S. patent application Ser. No. 29/213,754, filed Sep. 23, 2004, now U.S. Pat. No. D532,202, which is a continuation in part of U.S. patent application Ser. No. 10/843,135, filed May 11, 2004, now U.S. Pat. No. 7,331,731, which is a continuation in part of International application PCT/US03/27455, filed Sep. 4, 2003, which claims priority to U.S. Patent Application 60/408,321, filed Sep. 5, 2002; and (3) a continuation of U.S. application Ser. No. 29/231,487, filed Jun. 6, 2005, now U.S. Pat. No. D528,803, each of the above-referenced applications being incorporated herein by reference in their entirety.

FIELD OF THE INVENTION

The present invention relates generally to toothbrushes, and, more particularly, to a toothbrush which may have an oral care dispenser, such as a breath freshening, teeth cleaning gel capsule, and an oral care accessory, such as a toothpick.

DESCRIPTION OF THE RELATED ART

The advantages of good dental hygiene are well known. Often, however, toothbrushes are forgotten when one is traveling or away from home. Hotels, health care facilities, nursing homes, hospitals, daycare facilities, schools, airlines, etc. have a need for single use disposable or limited multiple use toothbrushes that may be economically supplied to and discarded by individuals without a toothbrush and/or a water supply. Such toothbrushes could be used in vending machines, or distributed in large quantities for simple, portable use from anywhere.

Various types of disposable, limited use, or portable toothbrushes are known in the art. For example, some toothbrush systems have attempted to meet some of these needs by providing toothpaste within the toothbrush itself, through an integrated channel, for distribution through the toothbrush and around the bristles. This approach can be less economical due to the added manufacturing costs of toothbrushes with integrated channels. In addition, the toothpaste in some of these integrated channel toothbrushes, not being properly sealed, has a tendency to become dry, hard and stale.

U.S. Pat. No. 6,135,274 shows an apparatus for brushing teeth that includes an outer bag, a toothbrush sealed within the outer bag, and a dispenser sealed within the outer bag and containing a mouth care solution. In use, the rupturable dispenser is squeezed or otherwise subjected to pressure while the toothbrush remains sealed within the outer bag. Unfortunately, the apparatus for brushing teeth requires an outer bag, increasing the cost of the apparatus, and fails to provide the rupturable dispenser and toothbrush as one complete, connected unit. The reference also fails to provide a toothpick mechanism for cleaning in between teeth, and which is also connected to the toothbrush.

U.S. Pat. No. 6,397,860 discloses a disposable, waterless tooth brushing assembly that includes a toothbrush, a non-foaming, saliva-activated, teeth-cleaning agent pre-applied to the bristles of the toothbrush, a small moistened disposable towel for user after teeth cleaning, and a compact, lightweight, two-layer heat-sealed packaging container for pre-use sanitary storage of the toothbrush and towel. Like U.S. Pat. No. 6,135,274, the assembly of U.S. Pat. No. 6,397,860 requires a packaging container, increasing the cost of the assembly, and fails to provide a rupturable dispenser and toothbrush as one complete, connected unit. The reference also fails to provide a toothpick mechanism for cleaning in between teeth, and which is also connected to the toothbrush.

Published U.S. application 2002/0106234 discloses a chewable toothbrush made of a flexible shell with bristles coupled to the shell and a chewable centerpiece disposed within the shell interior. A burstable capsule is disposed adjacent to the chewable centerpiece within the shell interior and maintains a digestible fluid.

None of the toothbrush assemblies of the related art includes a rupturable dispenser containing a dentifrice, a toothpick, and a toothbrush as one complete, connected unit or the various other combinations of oral care members and materials, later described. Thus, there is a need in the art for a waterless, toothbrush having a toothpick connected thereto to enable cleaning in between teeth or other accessory, and a dispenser containing a dentifrice or other oral care material and being connected in the bristle or cleaning element portion of the toothbrush for dispensing the dentifrice to the teeth to provide teeth cleaning and breath freshening or other oral care benefits.

SUMMARY OF THE INVENTION

The present invention solves the problems of the related art by providing in one embodiment a waterless toothbrush having a toothpick connected thereto to enable cleaning in between teeth, and a rupturable dispenser containing a dentifrice and being connected in the bristle portion of the toothbrush for dispensing the dentifrice to the teeth to provide teeth cleaning and breath freshening, all of which deliver a cleaning, polishing, whitening, between teeth cleaning, and breath freshening action in addition to enhancing the cleaning efficiency of a typical disposable or limited use toothbrush. The toothbrush of the present invention in this embodiment combines three benefits into one toothbrush: (1) tooth surface cleaning provided by the toothbrush bristles or other cleaning elements and the dentifrice in the rupturable dispenser; (2) between teeth cleaning provided by the toothpick; and (3) breath freshening provided by the dentifrice in the rupturable dispenser.

As embodied and broadly described herein, the present invention is broadly drawn to an oral care toothbrush, preferably comprising: a handle having an oral care head mounted to one end of the handle with an oral care accessory mounted to an opposite end of the handle. A plurality of oral care elements such as cleaning/massage elements, which could be bristles, extend outwardly from the outer surface of the head. The head also includes structure for dispensing oral care material in the oral care field of the head.

In a preferred practice of the invention the oral care toothbrush is characterized by its small size and light weight so that it is readily adaptable for travel use. The oral care toothbrush is preferably capable of having multiple functions by including an accessory as part of the toothbrush such as a toothpick, dental floss or tongue cleaner.

In one practice of this invention the oral care toothbrush includes a toothpick formed at one end of the handle; and a head connected at another end of said handle, said head having a bristle block that includes a plurality of bristles and retains a gel capsule therein, the gel capsule containing a mouth care solution. In further embodiments, the gel capsule can be replaced by a quantity of toothpowder, toothpaste or a tooth cleaning gel dentifrice, to provide the cleaning benefits of the dentifrice within the rupturable dispenser.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description. It is to be understood that both the foregoing general description and the following detailed description are exemplary and explanatory only and are not restrictive of the invention, as claimed.

Among the advantages of various practices of the invention are that the size and configuration of the toothbrush allows discreet hygienic use, such as no fingers in the mouth, adapting it to be readily used in public areas. Such uses could be done without the need for a sink or fountain or other source of water.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF EMBODIMENTS OF THE INVENTION

Figure 1:
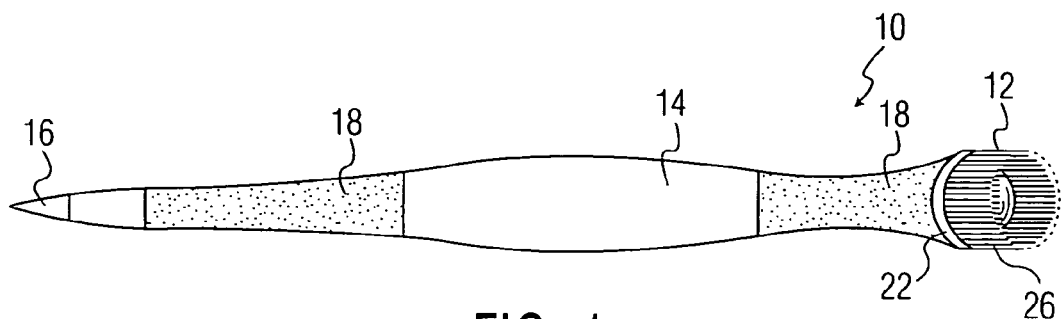
FIG. 1 is a front elevational view of an oral care toothbrush with a toothpick and a breath freshening, teeth cleaning gel capsule connected thereto in accordance with an embodiment of the present invention.

The following detailed description of the invention refers to the accompanying drawings. The same reference numbers in different figures identify the same or similar elements. Also, the following detailed description does not limit the invention. Instead, the scope of the invention is defined by the appended claims and equivalents thereof.

FIGS. 1-4 illustrate one practice of the present invention wherein an oral care toothbrush 10 includes a head 12 and a handle 14. Head 12 may be a refill head and thus be removably connected to handle 14, or head 12 may be permanently connected to head 12 within the practice of the present invention.

The majority of handle 14 and a portion of head 12 may be molded from a variety of rigid materials, including plastics, resins, etc., such as, for example, polypropylene. An end portion of handle 14, opposite the end head 12 is attached to an accessory, preferably a toothpick 16 formed of a resilient and soft thermoplastic elastomer. Toothpick 16 may be a refill and thus be removably connected to handle 14, or toothpick 16 may be permanently connected to handle 14 within the practice of the present invention. Toothpick 16 provides a mechanism for spot cleaning between teeth. Forming toothpick 16 of a soft elastomer provides more comfortable interproximal cleaning between teeth. Toothpick 16 could, however, be made of a stiff rigid material similar to the main portion of handle 14, or could simply be a rubber or elastomeric pick adhered or otherwise mounted to the end of handle 14.

Portions 18 of handle 14 may also be formed of a resilient and soft thermoplastic elastomer. The thermoplastic elastomer which forms toothpick 16 and handle portions 18 may be a thermoplastic vulcanate (TPV) consisting of a mixture of polypropylene and EPDM (ethylene propylene diene monomers) which is available as SANTOPRENE (brand), described in U.S. Pat. No. 5,393,796, or VYRAM (brand), another TPV consisting of a mixture of polypropylene and natural rubber. Both SANTOPRENE and VYRAM (brands) are elastomers marketed by Advanced Elastomer Systems. Other suitable elastomers include KRATON, a brand of styrene block copolymer (SBC) marketed by Shell, and DYNAFLEX G 2706 (brand), a thermoplastic elastomer marketed by GLS Corporation and which is made with KRATON (brand) polymer.

Handle 14 may further include dimples, bumps, or ridges protruding from portions of its surface, and providing a decorative appearance to handle 14 and enhanced gripping of handle 14 during use of toothbrush 10. The dimples may be formed from the same material as soft elastomer portions 18 of handle 14 or from the same material as the majority of handle 14 (e.g., a rigid material such as polypropylene). All or part of handle 14 could be made of any suitable material, such as plastic, wood, metal or various natural materials which are biodegradable. Preferably handle 14 is made of a generally flat or oval shape rather than cylindrical in its gripping portion which would be between the spaced elastomer portions 18,18 to facilitate the gripping of the handle.

Figure 4:
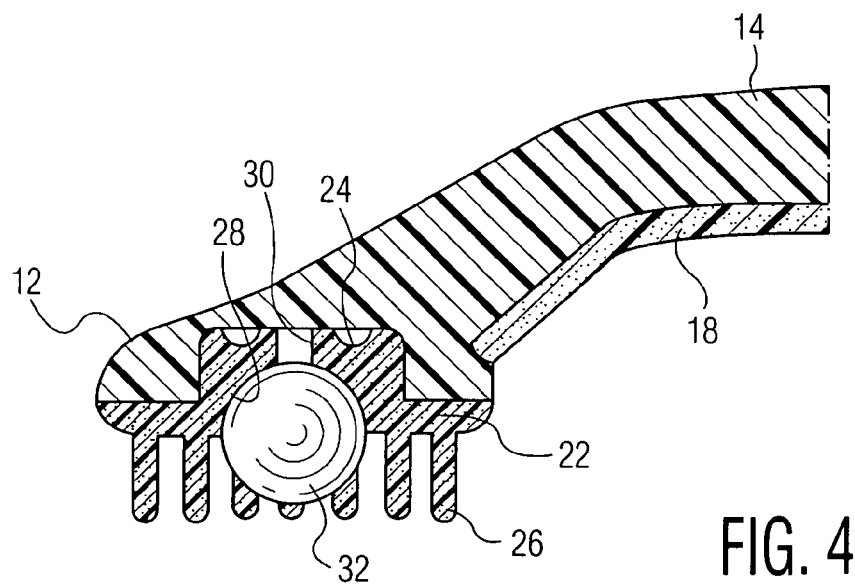
FIG. 4 is a fragmental, cross-sectional view of the head of an oral care toothbrush shown in accordance with this invention.

As shown in FIG. 4 another portion of head 12, defining a bristle or cleaning element block 22 of head 12, may also be formed of a resilient and soft thermoplastic elastomer, such as the thermoplastic elastomer used to form handle portions 18. Cleaning block 22 may include one or more depressions 24 provided in a surface 30 thereof with an opening 30 therein that provides a cushioning effect to a rupturable dispenser, preferably a gel capsule 32, contained therein, as described more fully below. Cleaning block 22 further includes a multitude of cleaning elements which could be conventional filament, preferably nylon, or elastomeric bristles or fingers 26 extending integrally outwardly from the outer surface of head 12. In the illustrated embodiment as best shown in FIG. 4, all of the cleaning elements 26 extend outwardly from the outer surface of block 22 the same distance so as to create a generally flat surface. Alternatively, however, some elements 26 may be shorter or longer than other elements 26. The variable length of the cleaning elements 26 is illustrated by the dotted out tips 26a in FIG. 14, with only body portions 26b of the cleaning elements 26 shown in solid lines for purposes of clarity and to focus on the variable nature of such elements.

The term "cleaning elements" as used herein is intended to be used in a generic sense as cleaning elements or massage elements arranged in a circular cross-section shape or any type of desired shape, including straight portions or sinusoidal portions. It is to be understood that the specific illustration of the cleaning elements is merely for exemplary purposes. The invention can, however, be practiced with various combinations of the same or different configurations (such as stapled, in-mold tufting (IMT) bristle technology as disclosed in U.S. Pat. Nos. 5,609,890, 5,390,984, and 5,533,791, the disclosures of which being incorporated by reference herein in their entirety, etc.) and/or with the same or different bristle materials (such as nylon bristles, spiral bristles, rubber bristles, etc.). Similarly, while FIGS. 1-4 illustrate the cleaning elements 26 to be generally perpendicular to the outer surface of head 12, some or all of the cleaning elements 26 may be angled at various angles with respect to the outer surface of head 12. It is thereby possible to select the combination of configurations, materials and orientations to achieve specific intended results, such as enhanced cleaning, tooth polishing, breath freshening, tooth whitening and/or massaging of the gums.

As stated above, the cleaning block 22 may include one or more depressions 24 which are designed to receive and retain an oral care dispenser, such as a rupturable gel capsule 32 therein. The one or more depressions 24 can be varied in size so as to accommodate not only varying size dispensers 32, but varying quantities of toothpowder, a toothpaste or tooth cleaning gel dentifrice or other oral care material, for delivery to the dentiture as the elements 26 extending from the block 22 are applied thereto, during use of the present invention such that the oral care material enhances the cleaning of the dentiture by the cleaning elements. While the present invention can be manufactured containing a packed toothpowder, toothpaste or tooth cleaning gel dentifrice and used repeatedly by the user refilling the dispenser with toothpowder, toothpaste or tooth cleaning gel dentifrice, it is preferably used with one or more gel capsules 32 contained therein. Most preferably the present invention is used with a single gel capsule 32, supplied therewith, so as to be most easily transported, used, and subsequently disposed of; however, it may also be used repeatedly with replaceable gel capsules 32, and then disposed of.

It is preferred that the depression is in the form of a cushioned socket 28 sized and shaped to receive and retain the gel capsule 32, without premature rupture of the gel capsule 32 prior to use thereof during application of the bristle block 22 to the dentiture and brushing thereof. Cushioning socket 28 opening 30, and the material making up bristle block 22 provide a cushioning effect for gel capsule 32 to prevent gel capsule 32 from rupturing prior to use.

Gel capsule 32 holds and applies a mouth care solution onto bristles 26 of toothbrush head 12. The mouth care solution may be a toothpaste, a gel, a mouthwash, or similar dentifrice or oral hygiene product, or a combination of the same contained in the rupturable capsule 32. Preferably gel capsule 32 is a liquid-filled gel capsule having frangible, thin walls that easily rupture or burst when rubbed against the teeth, or dissolve when mixed with the saliva of a user. The materials making up gel capsule 32 and the oral or mouth care solution contained therein preferably are consumable by the user of toothbrush 10, eliminating the need for water, a sink, or a waste receptacle to expectorate the gel capsule 32 or its contents. The mouth care solution remains in gel capsule 32 until toothbrush 10 is ready for use. Preferably, gel capsule 32 is fully sealed, helping the mouth care solution to remain fresh until use.

In use, gel capsule 32 would be pressed against the teeth and burst or rupture or dissolve, applying the mouth care solution over cleaning elements 26. The user then may brush their teeth with toothbrush 10. The user may also use toothpick 16 to clean between teeth, either before or after brushing. After the user has used toothbrush 10, one may, but not necessarily, then easily and economically dispose of toothbrush 10.

In one preferred aspect of the present invention, the entire structure of toothbrush 10, including head 12, handle 14, and toothpick 16, is molded as one integral structure, using a conventional two-component injection molding operation typically used in the manufacture of toothbrushes. This enables toothbrush 10 to be economically and quickly manufactured. Although toothbrush 10 may have a variety of sizes and dimensions, it is preferred that toothbrush 10 have a small profile, with head 12 being small enough to cover one tooth at a time and handle being thinner than conventional, everyday toothbrush handles. Toothbrush 10 is thus readily portable or space saving.

The toothbrush 10 of the present invention provides many benefits, including the cosmetic benefits of brushing one's teeth in a form that can be used when one is away from home, and away from a water supply. The cosmetic benefits achieved by the toothbrush 10 of the present invention include the cleaning of debris between teeth with toothpick 16, broad tooth surface cleaning (particularly the front teeth) with cleaning elements 26 and the mouth care solution of gel capsule 32, and breath freshening with the mouth care solution of gel capsule 32.

In addition to the cosmetic benefits, the toothbrush 10 of the present invention also provides economic benefits in the form of an inexpensive toothbrush that is both quickly and economically manufactured. Toothbrush 10 also provides a mechanism for maintaining oral health, without the need for toothpaste, water, mouth wash, and containers to hold the same. Thus, toothbrush 10 is also very convenient to use.

Although FIGS. 1-4 illustrate a manually-operated, disposable toothbrush, the present invention may also be practiced where the head includes one or more power or electrically operated movable sections carrying cleaning elements. Such movable section may oscillate in a rotational manner or may oscillate linearly in a longitudinal direction with respect to the longitudinal axis of the head or may oscillate linearly in a lateral or transverse direction with respect to the longitudinal axis of the head. The movable section may oscillate in and out in a direction toward and away from the outer surface of the head. The movable section may rock back and forth with respect to the outer surface of the head. The movable section may rotate continuously in the same direction, rather than oscillate. Any suitable drive mechanism may be used for imparting the desired motion to the movable section. Where plural movable sections are used, all of the movable sections may have the same type and direction of movement, or combinations of different movements may be used.

In accordance with one aspect of this invention the cleaning elements may be in the form of bristles made from conventional materials, such as nylon, as well as from a combination of materials so as to provide the proper stiffness in an economical manner. For example, the cleaning elements could be made of a flexible resilient material, such as TPE and a lesser expensive material such as LLDPE (linear low density polyethylene) or EVA (ethylene vinyl acetate) or a TPE. The cleaning elements could be made of a blend of TPE and either LLDPE, EVA, or polypropylene. Preferably, the two materials are combined to provide a stiffness of less than 600 MPa. The blend of materials would give the properties of conventional nylon bristles, while offering reduced costs. For example, there would be lower manufacturing costs by injection molding instead of conventional bristle tufting. Alternatively the resilient material could be a single material, such as hard TPE (i.e. Shore A 80 hardness), straight LLDPE or straight EVA.

The cleaning elements may be of any desired shape. For example, the cleaning elements could be of cylindrical shape having a uniform diameter throughout their length. Alternatively, the cleaning elements could taper from the root of each cleaning element where it extends from head 22 to its outer cleaning end. Since a preferred practice of the invention is to provide a small lightweight toothbrush the dimensions of the various components of toothbrush 10 are preferably small. Thus, for example, each cleaning elements may extend outwardly from the outer surface of cleaning block 12 a distance no greater than 10 mm and preferably no greater than 8 mm and most preferably no greater than 6 mm. Where tapered cleaning elements are used the root diameter should be no greater than 1.5 mm, preferably no greater than 1 mm, most preferably no greater than 0.7 mm or no greater than 0.5 mm or no greater than 03. mm. The diameter could then decrease in size to no greater than 0.2 mm at a distance of no greater than 6 mm from the base of the cleaning element. The taper relationship of diameter at a distance location above the root diameter could be a range of no greater than 1 mm at a distance of no greater than 10 mm, preferably no greater than 0.6 mm at a distance of no greater than 8 mm, most preferably no greater than 0.2 mm at a distance of no greater than 6 mm. Preferably, the length of the entire toothbrush 10 is no greater than 5 inches, preferably no greater than 4 inches, and more preferably no greater than 3.75 or 3 or 2.50 inches, and may be in the range of 2 to 4 inches.

Figure 14:
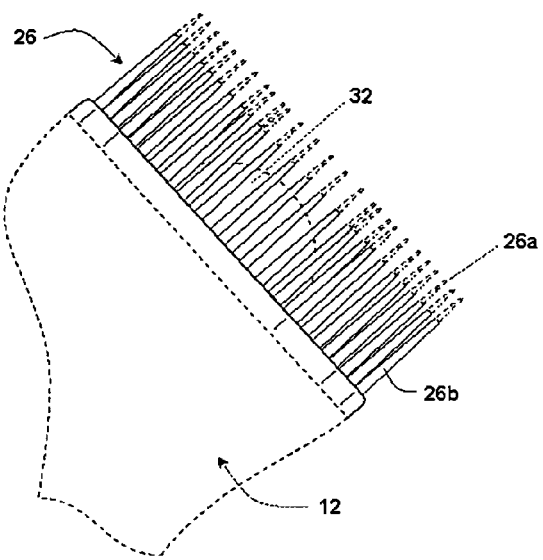
FIG. 14 is a side view of a head of an embodiment of the invention with only portions of the cleaning elements shown in solid lines for purposes of focus and clarity.

As illustrated in FIGS. 1 and 4 the cleaning elements define a cleaning field in the head and the dispenser 32 is mounted within this cleaning field. The cleaning elements 26 preferably extend outwardly from the cleaning block 22 to be approximately flush with the outer surface of the gel bead or capsule 32, as shown in FIG. 4. The invention, however, can also be practiced where the cleaning elements extend either a greater distance or a lesser distance than the dispenser 32 as shown in FIG. 14. Since toothbrush 10 is intended to be both small and lightweight, it is preferred that toothbrush 10 weigh no more than 3 grams. The small size is such that it can be held completely within the palm of an adult user. Head 12 is of a size that it would correspond to the size of an individual tooth or an individual tooth and the interproximal areas. Head 12 could be made of any suitable shape and is preferably of circular or oval shape having a maximum lateral dimension or diameter of no greater than 13 mm, preferably no greater than 12 mm and most preferably no greater than 11 mm. Where head 12 is of non-circular shape its maximum lateral dimension is 14 mm.

Figure 2:
FIG. 2 is a side elevational view of the toothbrush shown in FIG. 1.

As shown in FIG. 2 head 12 is preferably at an angle between 0° and 90° to the longitudinal axis of handle 14. The preferred angle is from 20° to 70° and more preferably from 30° to 60°. The cleaning elements could be perpendicular to the outer surface of head 12 or could also be at an angle to the outer surface such as in the range of 60° to 90° or in the range of 75° to 90°.

In one practice of the invention the cleaning elements could be hollow, such as hollow bristles, which are capable of absorbing a medicament by capillary action. Such practice of the invention would be particularly useful for children where a medicament or some form of flavor could be dispensed from the hollow cleaning elements. It is also possible to leach antibacterial material from the cleaning elements. In one practice of the invention where the cleaning elements are used to dispense oral care materials the cleaning elements themselves may be considered as the oral care dispensers without requiring additional dispensers such as capsule 32.

Where specific parameters and characteristics have been given for cleaning elements, the invention could be practiced where other cleaning elements do not include those parameters and characteristics.

Figure 5:
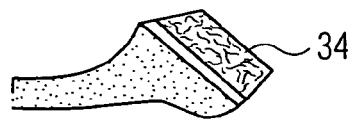
FIGS. 5-6 are side elevational views of other forms of heads for an oral care toothbrush in accordance with this invention.
Figure 6:
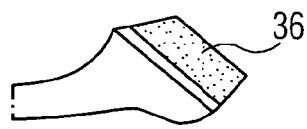

FIGS. 5-6 show other variations in the practice of this invention wherein the cleaning elements are in the form of a single mass having an irregular outer surface. As shown in FIG. 5 the mass 34 is similar to that of "steel wool" as used in household cleaning or could be part of Velcro® formations, such as hooks or loops.

FIG. 6 shows a variation where the cleaning element 36 is of a single mass of foam for cotton which could be used as a swab for oral care material. The outer surface of the swab could be generally planar or could have surface irregularities. In such practice of the invention the cleaning element 36 could be impregnated with the oral care material or could be dipped into oral care material so as to absorb the material and thereby the cleaning element 36 would also function as the oral care dispenser. Such swab type cleaning elements are gentle for children, particularly infants.

Figure 7:
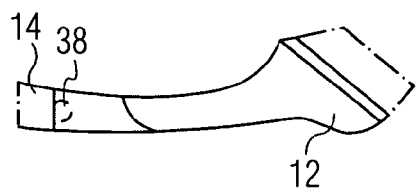
FIG. 7 is a fragmental side elevational view showing a head detachably mounted to the handle in accordance with a further practice of this invention.

The invention could be practiced where the various components of the toothbrush 10 are segmented for manufacturing and assembly purposes. Such segmented components could also be detachably connected together so as to permit the interchangeability of the components thereby providing the possibility for the substitution of different components in the combination. Thus, the head 12 could be detachably connected to the handle 14. FIG. 7, for example, illustrates head 12 to be detachably mounted to handle 14 by a snap fitting 38 which may be of any suitable construction as is known to those of ordinary skill in the art.

The concept of a detachable interconnection may also be used wherein the dispenser 32 is detachably mounted in the head 12 or wherein the oral care accessory, such as toothpick 16, is detachably mounted to handle 14. Thus, as later described with respect to FIGS. 12 and 13 the toothbrush and its various components could be packaged wherein the same package includes a plurality of toothbrushes and/or a plurality of different components such as heads, dispensers or accessories.

Figure 8:
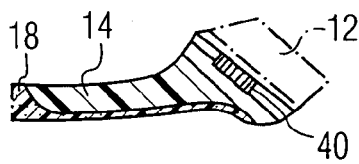
FIG. 8 is a fragmental cross-sectional elevational view showing a vibrating toothbrush head in accordance with this invention.

FIG. 8 shows a further practice of the invention wherein a piezoelectric crystal 40 is provided in the handle 14 at the junction with head 12 so as to cause the head 12 to vibrate during use. Alternatively the head 12 could be mounted to a rotatable shaft extending from the handle and having an eccentric weight on the shaft to cause the head to vibrate.

Figure 3:
FIG. 3 is a rear elevational view of the toothbrush shown in FIGS. 1-2.
Figure 9:
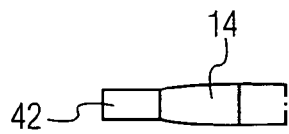
FIGS. 9-10 are fragmental front elevational views partly broken away of portions of a handle in accordance with yet another practice of this invention.

Although FIGS. 1-3 illustrate an oral care accessory 16 in the form of a toothpick, other types of accessories 42 could be used as schematically shown in FIG. 9. As illustrated therein such accessory 42 would be mounted to the end of handle 14 similar to the mounting of toothpick 16. Such mounting could be detachable or of a permanent nature. Examples of such oral care accessories include tongue cleaners, floss holders or an interproximal brush. Similarly, the accessory could be of a swab or foam type similar to the cleaning element 36 of FIG. 6 or could be of the single mass of roughened material such as the cleaning element 34 of FIG. 5.

Figure 10:
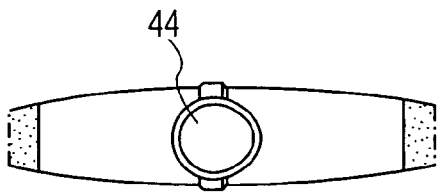

FIG. 10 shows another variation of the invention wherein the toothbrush is particularly adapted for use by children. Such use is enhanced by providing any suitable ornament or caricature 44 on the toothbrush, such as on the handle or on any other suitable location including the backside of the head. Such ornament 44 could be detachably mounted so that it could be kept by the child after the rest of the toothbrush is thrown away. Other aspects of the invention which make it desirable for use by children include the possibilities of dispensing various types of oral care materials including materials having special flavors, tooth numbing materials, anti-sensitive materials or various medicaments.

The toothbrush could also be made of various colors for different parts of the toothbrush. For example, soft elastomer 18 could be made of a different, such as a contrasting, color with respect to the remainder of handle 14 which would be made of a rigid material. Similarly, the head 12 could be made of a different color than the rigid portion of the handle and/or the soft elastomer portions 18. The cleaning elements 26 could be made of distinct colors and the dispenser 32 could also be made of a distinct color. Along the same lines the accessory such as toothpick 16 or other accessory 42 could be made of a distinct color. These various colors could be contrasting or complementary with each other. Thus, for example, the various colors could differ only slightly in color or shade.

Figure 11:
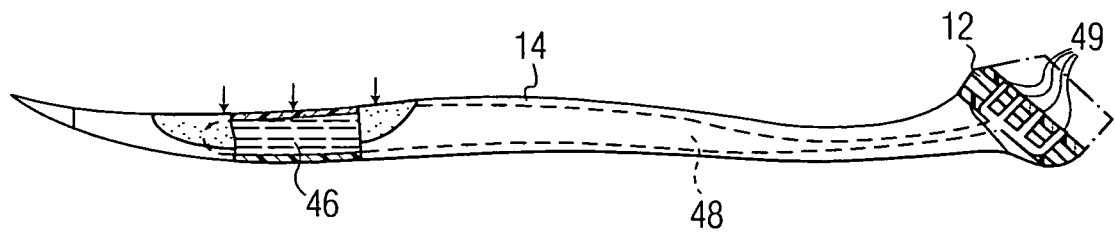
FIG. 11 is a side elevational view partly in section of yet another toothbrush in accordance with this invention.

FIG. 11 illustrates another practice of the invention wherein the handle 14 has a hollow chamber 46 in which the oral care material could be contained. Chamber 46 leads to a passageway 48 which extends to the head 12 such as terminating in a plurality of branches 49 at the outer surface of head 12 within the cleaning field. In order to dispense the oral care material located in the chamber or reservoir 46 handle 14 would have sufficient resiliency so that it can be squeezed thereby forcing the material from the handle to the head into a dispensing cavity or one or more dispensing openings.

Figure 15:
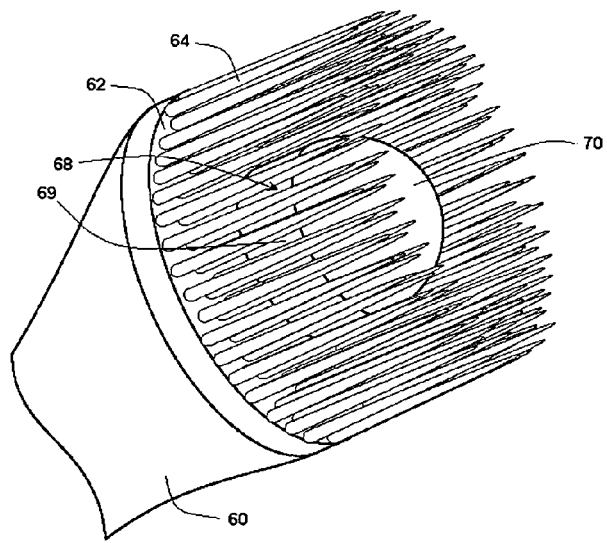
FIG. 15 is a perspective view of one embodiment of a toothbrush head of the invention.
Figure 16:
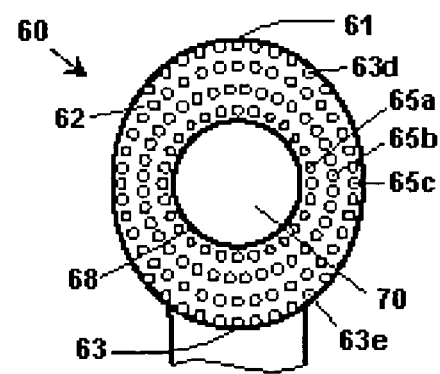
FIG. 16 is a close up perspective front view of the head of FIG. 15.

FIGS. 15 and 16 illustrate a head 60 according to another embodiment of the invention, the head 60 having an outer surface 62, a plurality of cleaning elements 64 extending from a portion of the outer surface 62, and a raised socket 68 extending from another portion of the outer surface 62. The socket 68 is preferably formed from the same material as the outer surface 62, and is preferably integrally formed with the outer surface such as by molding or the like. The socket 68 extends outwardly relative to the outer surface 62 by an upstanding wall 69, and includes a seat to accommodate an oral care dispenser such as a bead or capsule 70 as discussed herein. The raised socket 68 positions the dispenser 70 closer to the edges of the cleaning elements 64 to facilitate contact between the dispenser 70 and the user's teeth and to encourage rupturing of the dispenser 70 early in the brushing process. The socket may also position the dispenser 70 beyond the cleaning elements 64 as discussed above, which would encourage even greater and immediate contact with the user's teeth.

The cleaning elements 64 may comprise a variety of configurations as discussed above, such as a circular configuration as shown in FIG. 1. FIG. 16 illustrates an example of an oval configuration, wherein the cleaning elements 64 are arranged in a plurality of concentric rings 65a, 65b, 65c, surrounding the socket 68. One of such rings is a partial ring comprised of partial ring sections 65d, 65e defined along the upper and lower edges 61, 63 of the outer surface 62 of the head 60, which sections 65d, 65e comprise the equivalent of a so-called power tip that is designed to provide a cleaning edge that extends beyond the majority of the field of cleaning elements for increased efficacy.

Any suitable oral care products could be dispensed from the dispenser. Such products include, but are not limited to the gel capsule 32 as previously described and could contain toothpaste, tooth powder or could be a small vial of mouthwash having a gel, a powder or a liquid. Such a vial could be separately included in a package containing the toothbrush. The materials could be flavored and could be provided in sets of different flavors and/or different characteristics such as medicaments, numbing materials, etc.

Where the dispensers 32 are in the form of beads, different beads or capsules could be used with different colors/flavors to enhance consumer appeal. As described the capsule 32 could be an impregnated bead that burst. Suitable beads include those supplied by Mane Inc.

Any suitable methods may be used for forming toothbrush 10 and its various components. For example, multi-component injection molding could be used to integrally couple various components such as the cleaning elements and the head and/or the handle. This could be done in an automated or multiple step process. The handle could be rotocast blow molded to form a hollow squeeze handle that would be usable in the embodiment shown in FIG. 11.

Figure 12:
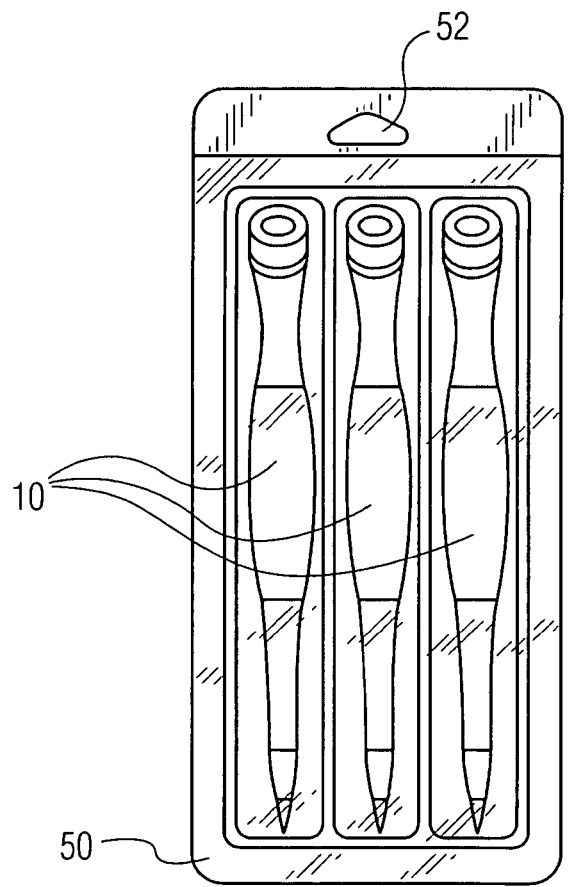
FIGS. 12-13 are front elevational views showing various forms of toothbrushes in accordance with this invention in the packaged or display condition.
Figure 13:
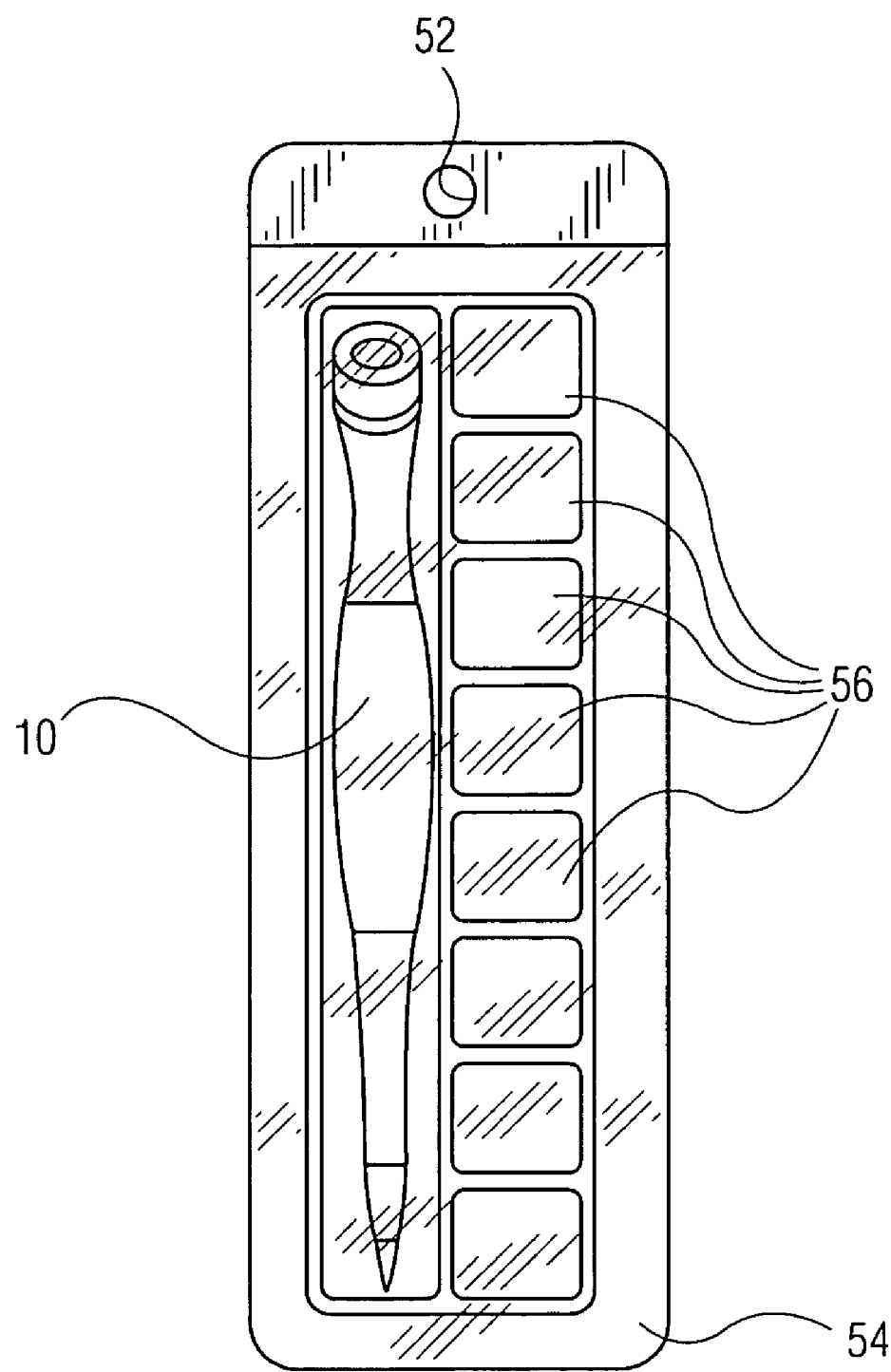

FIGS. 12-13 show different manners of packaging toothbrushes in accordance with this invention. As shown in FIG. 12, for example, a single package 50 could contain a plurality of toothbrushes 10 all of which could be the same or could differ from each other. The package 50 could be of any conventional construction, such as a blister pack, which might include a hole 52 to permit the package to be hung for display purposes.

FIG. 13 illustrates a variation wherein the package 54 includes one or more toothbrushes 10 and a plurality of other components 56 which could be accessories or dispensers or other components. The components could include a small vial of mouthwash. Preferably, the package 50 or 54 would be hermetically sealed to assure freshness. Such hermetic sealing is particularly desired to prevent moisture from reaching gel capsule 32 and causing the capsule to burst.

As is apparent the present invention provides an oral care toothbrush which is preferably small in size and portable and can be conveniently used away from home under circumstances, such as travel, where water is not readily available.

The invention could be practiced with a combination of various components which do not involve "toothbrush" usage. In that sense the invention is an oral care device or the like, rather than strictly being a toothbrush. Where used as a toothbrush or the like, the invention may have the advantages, because of the size and configuration, to allow discreet hygienic use, such as no fingers in the mouth, adapting it to be readily used in public areas.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A toothbrush comprising a handle having a longitudinal axis, a head mounted to one end of said handle, said head having an oral care element carrying portion having an outer planar surface, a plurality of oral care elements extending outwardly from said outer surface, and a dispenser housing an oral care material stored entirely in the oral care element carrying portion of the head and having a first portion disposed within the oral care element carrying portion of the head beneath the outer planar surface and a second portion disposed outside the head above the outer planar surface, wherein at least one oral care element extends at an angle to the longitudinal axis of the handle and the handle is free of oral care material.

2. The toothbrush of claim 1, wherein said angle is in the range of 0° to 90°.

3. The toothbrush of claim 1, wherein said angle is in the range of 30° to 60°.

4. The toothbrush of claim 1, wherein the plurality of oral care elements surrounds the dispenser in a circumferential fashion, and the shape of the head is consistent with the arrangement of oral care elements on the head.

5. A toothbrush comprising a handle having a longitudinal axis, a head mounted to a first end of said handle with the opposite end of said handle defining a second end, a central portion defined between the first and second ends, said head having an oral care element carrying portion having an outer planar surface, at least one oral care element extending outwardly from said outer planar surface, and a dispenser housing an oral care material stored entirely in the oral care element carrying portion of the head and having a first portion disposed within the oral care element carrying portion of the head beneath the outer planar surface and a second portion disposed outside the head above the outer planar surface, wherein the central portion of said handle is wider than the handle at the first and second ends and the handle is free of oral care material.

6. The toothbrush of claim 5, wherein the central portion is wider in a front view of the toothbrush.

7. The toothbrush of claim 6, wherein in a side view of the toothbrush, the head extends at an angle to the longitudinal, axis of the handle.

8. The toothbrush of claim 7, wherein the head extends upwardly relative to the longitudinal axis of the handle.

9. The toothbrush of claim 7, wherein the second end of the handle extends at an angle to the longitudinal axis of the handle.

10. The toothbrush of claim 9, wherein the head and second end each extend upwardly relative to the longitudinal axis of the handle.

11. The toothbrush of claim 5, further comprising a plurality of circumferentially arranged oral care elements surrounding the oral care material stored in the head.

12. The toothbrush of claim 11, wherein the head has an oval profile and the oral care elements further comprise a plurality of radially-spaced rows.

13. A toothbrush comprising a handle, a head mounted to one end of said handle, said head having an outer surface and a peripheral edge, a plurality of oral care elements extending outwardly from said outer surface, and a circular socket having a peripheral edge and provided in said outer surface and surrounded by said oral care elements for accommodating an oral care material therein, wherein the peripheral edges of the head and the socket have a similar profile and a diameter of the circular socket at the outer surface is greater than any radial distance defined between the socket peripheral edge and the head peripheral edge.

14. The toothbrush of claim 13, wherein the socket, oral care elements and head peripheral edge are coaxially aligned.

15. The toothbrush of claim 14, wherein the socket, oral care elements and head peripheral edge each have a rounded profile.

16. The toothbrush of claim 15, wherein the socket, oral care elements and head peripheral edge each have an oval profile.

17. The toothbrush of claim 13, wherein the socket is centrally located on the head and wherein the plurality of oral care elements further comprise a plurality of radially-spaced, circumferentially-arranged rows.

* * * * *